US011448629B2

(12) United States Patent
Do et al.

(10) Patent No.: US 11,448,629 B2
(45) Date of Patent: Sep. 20, 2022

(54) APPARATUS AND METHOD FOR DETERMINING LOCATION OF POLLUTANT SOURCE USING DRONE

(71) Applicant: AGENCY FOR DEFENSE DEVELOPMENT, Daejeon (KR)

(72) Inventors: Sangwon Do, Daejeon (KR); Jiyun Seo, Daejeon (KR); Hyunwoo Nam, Daejeon (KR); Myeongjae Lee, Daejeon (KR)

(73) Assignee: Agency For Defense Development, Daejeon (KR)

( * ) Notice: Subject to any disclaimer, the term of this patent is extended or adjusted under 35 U.S.C. 154(b) by 369 days.

(21) Appl. No.: 16/663,713

(22) Filed: Oct. 25, 2019

(65) Prior Publication Data

US 2020/0309756 A1 Oct. 1, 2020

(30) Foreign Application Priority Data

Apr. 1, 2019 (KR) .................. 10-2019-0037870

(51) Int. Cl.
*G01N 33/00* (2006.01)
*G05D 1/00* (2006.01)
(Continued)

(52) U.S. Cl.
CPC ....... *G01N 33/0062* (2013.01); *B64C 39/024* (2013.01); *G01N 33/0004* (2013.01); *G01N 33/0036* (2013.01); *G05D 1/0094* (2013.01); *G05D 1/102* (2013.01); *G05D 1/106* (2019.05); *B64C 2201/12* (2013.01)

(58) Field of Classification Search
CPC combination set(s) only.
See application file for complete search history.

(56) References Cited

U.S. PATENT DOCUMENTS

2007/0073486 A1* 3/2007 Tillotson ................. G01W 1/00 702/3
2016/0364989 A1* 12/2016 Speasl ................. G08G 5/0082

FOREIGN PATENT DOCUMENTS

CN 109633114 * 1/2019
CN 109376423 A * 2/2019
(Continued)

OTHER PUBLICATIONS

Human translation of CN-109376423 (Year: 2019).*
Machine translation of CN-109633114 (Year: 2019).*

*Primary Examiner* — Nathaniel J Kolb
(74) *Attorney, Agent, or Firm* — Knobbe Martens Olson & Bear LLP

(57) ABSTRACT

A method for determining a location of a pollutant source, comprises: obtaining wind direction information for a region of interest; measuring pollutant concentrations for a first plane of interest in the region of interest with a movement determined based on the wind direction information using a drone equipped with a chemical sensor, the first plane of interest being determined based on a current altitude of the drone; lowering by a predetermined descending distance an altitude of the drone from a descent position on the first plane of interest determined on the basis of a result of the measuring; and determining a pollutant source candidate area based on a location of the drone after the lowering if the lowered altitude of the drone is equal to or less than a predetermined reference altitude.

16 Claims, 11 Drawing Sheets

(51) Int. Cl.
 *G05D 1/10* (2006.01)
 *B64C 39/02* (2006.01)

(56) References Cited

FOREIGN PATENT DOCUMENTS

| | | |
|---|---|---|
| KR | 10-2013-0097832 A | 9/2013 |
| KR | 10-2016-0147577 A | 12/2016 |
| KR | 10-2018-0119445 A | 11/2018 |

* cited by examiner

APPARATUS AND METHOD FOR DETERMINING LOCATION OF POLLUTANT SOURCE USING DRONE

CROSS-REFERENCE TO RELATED APPLICATION

This application claims priority to Korean Patent Application No. 10-2019-0037870, filed on Apr. 1, 2019, the entire contents of which are incorporated herein by reference.

FIELD

The present disclosure relates to an apparatus and a method for determining a location of a pollutant source that generates a chemical pollutant cloud.

BACKGROUND

Chemical, biological and radiological (CBR) reconnaissance is to find out a location of a pollutant source that generates a chemical pollutant cloud by conducting reconnaissance in a region where pollution is expected and to find out a specific contour (pollutant boundary) of the pollutant region. The CBR reconnaissance is conducted in an urgent state, and thus needs to be conducted safely and quickly. However, since the CBR reconnaissance is conducted by chemical forces, scouts are exposed to CBR weapons that are fatal to human health.

Therefore, recently, researches have been conducted on a method using an unmanned device for exploring a pollutant region. For example, by exploring a pollutant region using an unmanned air vehicle such as a drone, various information on the pollutant region can be obtained without threat to safety of a researcher.

The information that can be obtained by the drone may include information on the location of the pollutant source in the pollutant region. It is possible to suppress expansion of the polluted area by accurately exploring the location of the pollutant source.

The disclosure of this section is to provide background information relating to the invention. Applicant does not admit that any information contained in this section constitutes prior art.

SUMMARY

In view of the above, the present disclosure provides an apparatus and a method for determining a location of a pollutant source, which is capable of determining a pollutant source candidate area based on a location of a drone if the altitude of the drone is equal to or less than a reference altitude when the drone descends by a descending distance from a descent position on a plane of interest in a region of interest.

In accordance with an aspect of the present disclosure, there is provided a method for determining a location of a pollutant source, the method comprising: obtaining wind direction information for a region of interest; measuring pollutant concentrations for a first plane of interest in the region of interest with a movement determined based on the wind direction information using a drone equipped with a chemical sensor, the first plane of interest being determined based on a current altitude of the drone; lowering by a predetermined descending distance an altitude of the drone from a descent position on the first plane of interest determined on the basis of a result of the measuring; and determining a pollutant source candidate area based on a location of the drone after the lowering if the lowered altitude of the drone is equal to or less than a predetermined reference altitude.

The method may further comprise: measuring pollutant concentrations for a second plane of interest determined based on the lowered altitude of the drone if the lowered altitude of the drone exceeds the reference altitude.

The measuring pollutant concentrations may include: advancing the drone in a first traveling direction determined on the basis of the wind direction information to measure the pollutant concentration; determining as a turning position a position at which the highest pollution concentration is detected by the drone among first positions at which the drone measures the pollutant concentrations while moving in the first traveling direction; and turning the drone at the turning position and advancing the drone in a second traveling direction substantially perpendicular to the first traveling direction to measure the pollutant concentration, wherein the movement includes a movement in the first traveling direction and a movement in the second traveling direction.

The lowering the altitude of the drone may include: determining as the descent position a position at which the highest pollution concentration is detected by the drone among second positions at which the drone measures the pollutant concentrations while moving in the second traveling direction; and lowering the altitude of the drone from the descent position by the predetermined descending distance.

The determining the pollutant source candidate area may include: measuring pollutant concentrations at a plurality of detection positions spaced from a center position determined based on the location of the drone after lowering, whose altitude is equal to or less than the predetermined reference altitude; and determining the pollutant source candidate area based on the pollutant concentrations at the plurality of detection positions.

The determining the pollutant source candidate area based on the pollutant concentrations at the plurality of detection positions may include: defining an area within a predetermined radial distance from the center position as the pollutant source candidate area if the pollutant concentrations measured at all of the plurality of detection locations are equal to or greater than a predetermined reference concentration; and if at least one of the pollution concentrations measured at the plurality of detection positions is not equal to or greater than the predetermined reference concentration, defining the pollutant source candidate area so that the pollutant source candidate area contains detection positions at which the measured pollutant concentrations are equal to or greater than the predetermined reference concentration, excluding other positions at which the measured pollutant concentrations are smaller than the predetermined reference concentration.

The determining the pollutant source candidate area based on the pollutant concentrations at the plurality of detection positions may include: obtaining a gradient of the pollutant concentrations at the plurality of detection positions; and determining the pollutant source candidate area based on the obtained pollutant concentration gradient.

In accordance with another aspect of the present disclosure, there is provided an apparatus for determining a location of a pollutant source, the apparatus comprising: a drone equipped with a chemical sensor for detecting concentration of pollution; and a control unit configured to control the drone, wherein the control unit controls the drone to measure pollutant concentrations for a first plane of interest in a region of interest with a movement determined based on wind direction information with respect to the region of interest, the first plane of interest being determined based on a current altitude of the drone, lowers an altitude of the drone from a descent position on the first plane of interest determined on the basis of the measurement result by a predetermined descending distance, and determines a pollutant source candidate area based on a location of the drone if the lowered altitude of the drone is equal to or less than a predetermined reference altitude.

The drone may comprise a lidar configured to obtain the wind direction information with respect to the region of interest.

In accordance with the aspects of the present disclosure, it is possible to safely explore a chemical pollutant cloud by determining the location of a pollutant source using the drone.

Further, by exploring the chemical pollutant cloud based on the plane determined based on the altitude of the drone, the search accuracy for the chemical pollutant cloud can be increased. As a result, it is possible to correctly determine the location of the pollutant source in the chemical pollutant cloud.

BRIEF DESCRIPTION OF THE DRAWINGS

The objects and features of the present disclosure will become apparent from the following description of embodiments, given in conjunction with the accompanying drawings, in which.

DETAILED DESCRIPTION OF THE EMBODIMENTS

The advantages and features of embodiments and methods of accomplishing these will be clearly understood from the following description taken in conjunction with the accompanying drawings. However, embodiments are not limited to those embodiments described, as embodiments may be implemented in various forms. It should be noted that the present embodiments are provided to make a full disclosure and also to allow those skilled in the art to know the full range of the embodiments. Therefore, the embodiments are to be defined only by the scope of the appended claims.

In describing the embodiments of the present disclosure, if it is determined that detailed description of related known components or functions unnecessarily obscures the gist of the present disclosure, the detailed description thereof will be omitted. Further, the terminologies to be described below are defined in consideration of functions of the embodiments of the present disclosure and may vary depending on a user's or an operator's intention or practice. Accordingly, the definition thereof may be made on a basis of the content throughout the specification.

A term such as "unit" or the like disclosed in the specification indicates a unit for processing at least one function or operation, and may be implemented in hardware, software or in combination of hardware and software.

Figure 1:
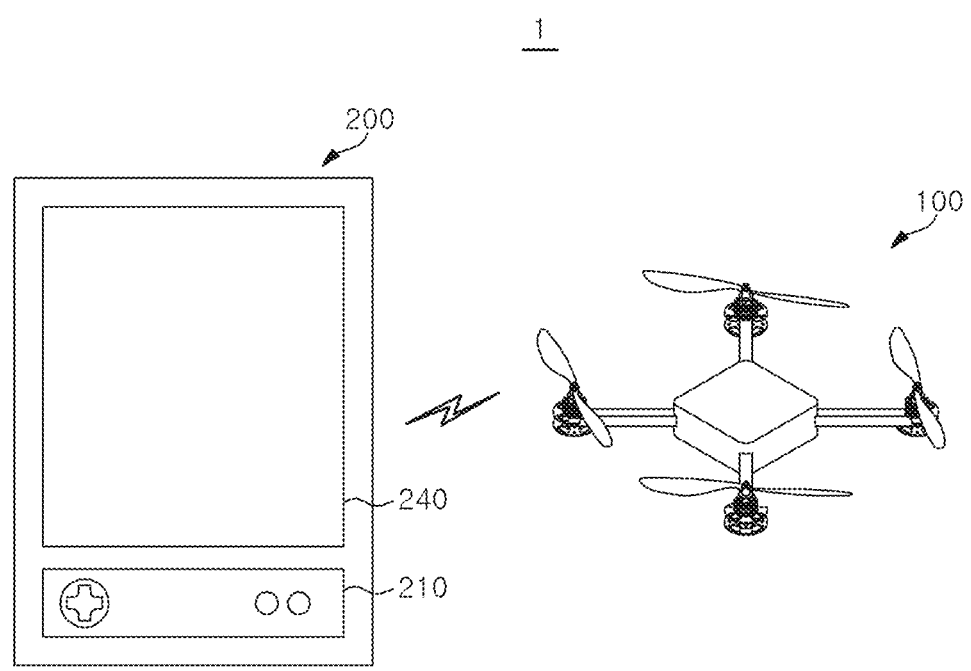
FIG. 1 shows an apparatus for determining a location of a pollutant source according to one embodiment of the present disclosure.
Figure 2:
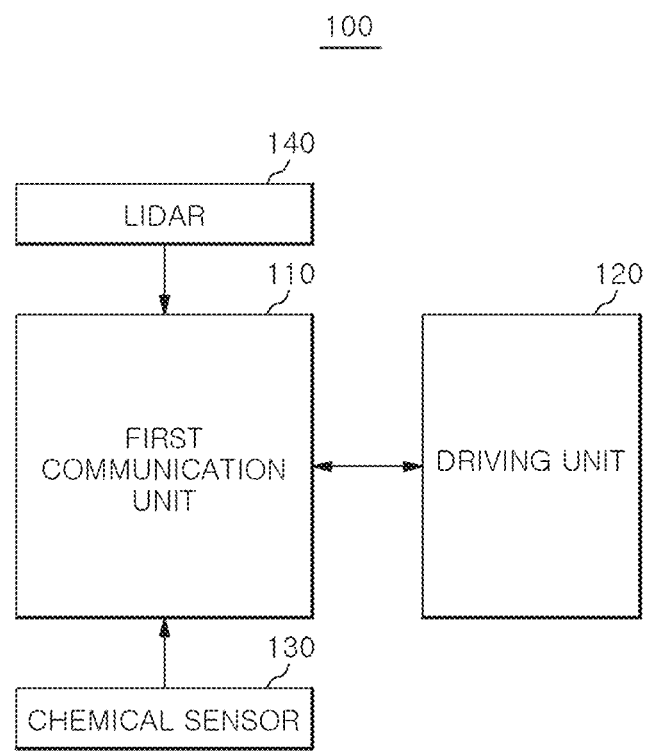
FIG. 2 is a functional block diagram of a drone according to one embodiment of the present disclosure.
Figure 3:
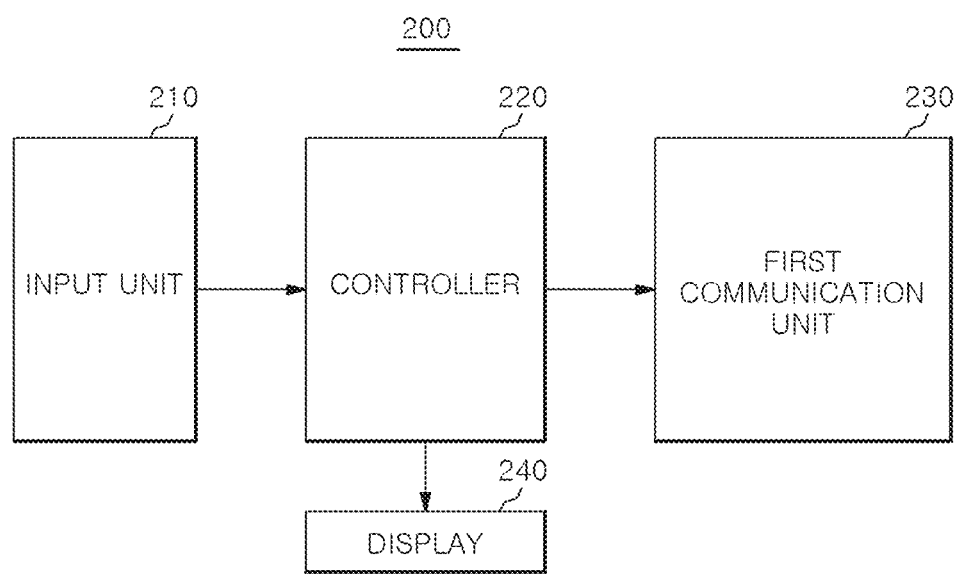
FIG. 3 is a functional block diagram of the apparatus for determining the location of a pollutant source according to one embodiment of the present disclosure.

FIG. 1 shows an apparatus for determining the location of a pollutant source according to one embodiment of the present disclosure. FIG. 2 is a functional block diagram of a drone according to one embodiment of the present disclosure. FIG. 3 is a functional block diagram of the apparatus for determining the location of a pollutant source according to one embodiment of the present disclosure.

The apparatus for determining the location of a pollutant source indicates an apparatus for determining the location of a pollutant source that generates a chemical pollutant cloud as a region of interest (ROI) and that exists in the ROI.

The pollutant source discharges chemical substances harmful to human health in a gaseous or a liquid state, and the discharged chemical substances can generate a chemical pollutant cloud in the atmosphere. If the pollutant source continues to release the chemical substances, the area of chemical pollutant cloud may gradually expand, and the scale of the damage may also increase. Therefore, in order to minimize the damage caused by the chemical pollutant cloud, it is necessary to quickly remove the chemical pollution source in the chemical pollutant cloud.

However, when the inner side of the chemical pollutant cloud is directly explored by a researcher, the researcher is completely exposed to the chemical substances in the chemical pollutant cloud. Since the chemical substances in the chemical pollutant cloud are generally harmful to human health, the exposure thereto can seriously threaten the safety of the researcher.

Therefore, an unmanned device can be used to explore the inner side of the chemical pollutant cloud. If the exploring device is remotely controlled manually, it is required for a user to perform accurate control in order to explore the location of the pollutant source in the chemical pollutant cloud. In other words, the accuracy of exploration of the location of the pollutant source in the chemical pollutant cloud may be affected by a user's skill level or the like.

On the other hand, the exploring device can automatically explore the inner side of the chemical pollutant cloud based on a predetermined control algorithm. The apparatus for determining the location of the pollutant source according to the present embodiment, is capable of determining a pollutant source candidate area (an area where the pollutant source may exist) based on a location of a drone if the altitude of the drone is equal to or less than a reference altitude when the drone descends by a descending distance from a descent position on a plane of interest in a region of interest.

Referring to FIG. 1, an apparatus for determining the location of the pollutant source according to one embodiment of the present disclosure includes a drone 100 that flies in response to a control signal, and a control unit for transmitting a control signal to the drone 100.

The drone 100 is an unmanned air vehicle that is remotely controlled by a user automatically or manually without the user on board. The drone 100 flies in various known manners. In one embodiment, the drone 100 can fly by lift force generated by rotating an internal rotor. The flying technique of the drone 100 of the present disclosure is not limited to that in the above-described embodiment.

Referring to FIG. 2, the drone 100 according to the embodiment of the present disclosure includes a first communication unit 110, a driving unit 120, a chemical sensor 130, and a lidar 140.

The first communication unit 110 can communicate with a control unit to be described later. Therefore, the first communication unit 110 can adopt various known communication methods, e.g., the same communication method as that of the control unit. For example, the first communication unit 110 according to one embodiment can adopt a known communication method such as CDMA, GSM, W-CDMA, TD-SCDMA, WiBro, LTE, EPC, or the like and communicate with the control unit via a base station. On the contrary, a first communication unit 110 according to another embodiment can adopt a communication method such as wireless LAN, Wi-Fi, Bluetooth, Zigbee, Wi-Fi Direct (WFD), Ultra Wideband (UWB), Infrared Data Association (IrDA), Bluetooth Low Energy (BLE), Near Field Communication (NFC), or the like and communicate with the control unit within a predetermined distance. The communication method between the first communication unit 110 of the present disclosure and the control unit is not limited to that in the above-described embodiment.

The first communication unit 110 can transmit and receive information that is directly or indirectly related to the flying of the drone 100 to and from the control unit. For example, the first communication unit 110 according to one embodiment can receive a control signal for controlling the operation of the drone 100 from the control unit or transmit the information on the flight obtained during the flight to the control unit.

The driving unit 120 can generate lift force so that the drone 100 can fly. The driving unit 120 can generate the lift force in different manners corresponding to various flying techniques adopted by the drone 100. For example, the driving unit 120 according to one embodiment can generate lift force by rotating a rotor and a rotational blade provided at one end of the rotor.

The driving unit 120 can be driven by the control signal received by the first communication unit 110. For example, the driving unit 120 according to one embodiment can drive the drone 100 to start flight, to stop flight, to fly in a straight line, to change a direction, to lower an altitude, to hold a current position, or the like in response to the control signal.

The chemical sensor 130 can detect the presence of chemical substances defined as contaminants and the concentration of the chemical substances. The chemical sensor 130 is provided outside the drone 100 and exposed to a position that allows detection of the chemical substances in the atmosphere around the drone 100 in flight.

The chemical sensor 130 according to one embodiment may be implemented as a contact-type sensor. Therefore, the contact-type chemical sensor 130 may include a catalyst that is brought into contact with and reacts with chemical substances. For example, the catalyst of the contact-type chemical sensor 130 according to one embodiment burns in contact with the chemical substances, thereby increasing a temperature in the sensor. Accordingly, the contact-type chemical sensor 130 can detect the presence and the concentration of the chemical substance based on the changes in a resistance of an internal element due to the temperature increase. However, this is merely one embodiment of the contact-type chemical sensor 130, and the contact-type chemical sensor 130 of the present disclosure can be variously implemented within a technical idea in which the contact-type chemical sensor 130 makes contact with and detects the chemical substances.

On the contrary, the chemical sensor 130 according to another embodiment can be implemented as a non-contact type sensor. Therefore, the non-contact type chemical sensor 130 may include a light collecting unit for collecting light emitted from the chemical substances. For example, the light collecting unit of the non-contact type chemical sensor 130 according to one embodiment can obtain a spectrum of the collected light from the surrounding atmosphere, and the non-contact type chemical sensor 130 can detect the presence and the concentration of the chemical substances by comparing the obtained spectrum of the light with a reference spectrum. However, this is merely one embodiment of the non-contact type chemical sensor 130, and the non-contact type chemical sensor 130 of the present disclosure can be variously implemented within a technical idea in which the non-contact type chemical sensor 130 detects the chemical substances without contact therewith.

The lidar 140 can detect a wind direction and a wind speed around the drone 100. Therefore, the lidar 140 according to one embodiment can be implemented as a Doppler lidar 140 for detecting a wind direction and a wind speed using the Doppler effect in which a wavelength of a wave is converted when a wave source becomes relatively away from or close to an observer. On the other hand, the lidar 140 according to another embodiment can detect a wind direction and a wind speed based on a degree of non-uniformity of aerosol in the atmosphere.

Referring back to FIG. 1, the control unit can transmit a control signal for controlling flight of the drone 100 to the drone 100. At this time, the control signal can be inputted by a user's control command or can be automatically generated by an internal operation of the control unit.

Referring to FIG. 3, the control unit according to one embodiment of the present disclosure includes an input unit 210, a controller 220, a second communication unit 230, and a display 240.

The input unit 210 may be provided at the outer side of the control unit so that a user can input a control command. For example, the input unit 210 according to one embodiment may be disposed at a front surface of the control unit when viewed from the user.

The input unit 210 may be configured to receive the control command in various known manners. For example, the input unit 210 according to one embodiment includes a press-type button that senses user's press and receives a control command, a capacitive button that senses user's touch and receives a control command, or the like. In addition, the input unit 210 according to one embodiment may be implemented as a keyboard, a joystick, a track ball, a jog shuttle, or the like and receive the control command from the user.

The controller 220 can generate a control signal for controlling the operation of the drone 100. The controller 220 according to one embodiment can generate a control signal corresponding to a control command inputted through the input unit 210. For example, the controller 220 according to one embodiment can generate a flight start signal corresponding to a flight start command inputted through the input unit 210, a flight stop signal corresponding to a flight stop command, a straight flight signal corresponding to a straight flight command, a direction changing signal corresponding to a direction changing command, an altitude decreasing signal corresponding to an altitude decreasing command, a current position holding signal corresponding to a current position holding command, or the like.

On the other hand, the controller 220 according to another embodiment can generate a control signal for controlling the drone 100 based on a predetermined control algorithm. At this time, the controller 220 can input the information on the flight of the drone 100 received by the second communication unit 230 to be described later into the control algorithm and generate a control signal corresponding to an output value.

Hereinafter, it is assumed that the controller 220 generates a control signal based on the information on the flight, for convenience of description.

The controller 220 according to one embodiment may be implemented as an operation unit including a microprocessor. For example, the controller 220 may be implemented as a central processing unit (CPU), a graphic processing unit (GPU), or the like. At this time, the controller 220 may be implemented as a single microprocessor or as a single system on chip (SOC) in which a plurality of microprocessors is integrated.

The second communication unit 230 can communicate with the drone 100. Therefore, the second communication unit 230 can adopt various known communication methods, e.g., the same communication method as that of the drone 100. The communication method that can be adopted by the second communication unit 230 is the same as that adopted by the first communication unit 110 of the drone 100.

The second communication unit 230 can transmit and receive information that is directly or indirectly related to the flight of the drone 100 to and from the control device. For example, the second communication unit 230 according to one embodiment can transfer a control signal for controlling the operation of the drone 100 to the drone 100 or receive the information on the flight obtained during the flight from the drone 100.

The display 240 can display the information on the flight of the drone 100. For example, the display 240 according to one embodiment can display a flight path of the drone 100, a flight speed, a wind direction and a wind speed around the drone 100, a current temperature, map information, or the like.

Therefore, the display 240 according to one embodiment may be implemented as a cathode ray tube (CRT), a plasma display panel (PDP), a liquid crystal display (LCD), a light emitting diode (LED), an organic light emitting diode (OLED), or the like.

So far, the configuration of the apparatus for determining the location of a pollutant source has been described. Hereinafter, a method for determining the location of a pollutant source performed by the apparatus for determining the location of a pollutant source will be described.

Figure 4:
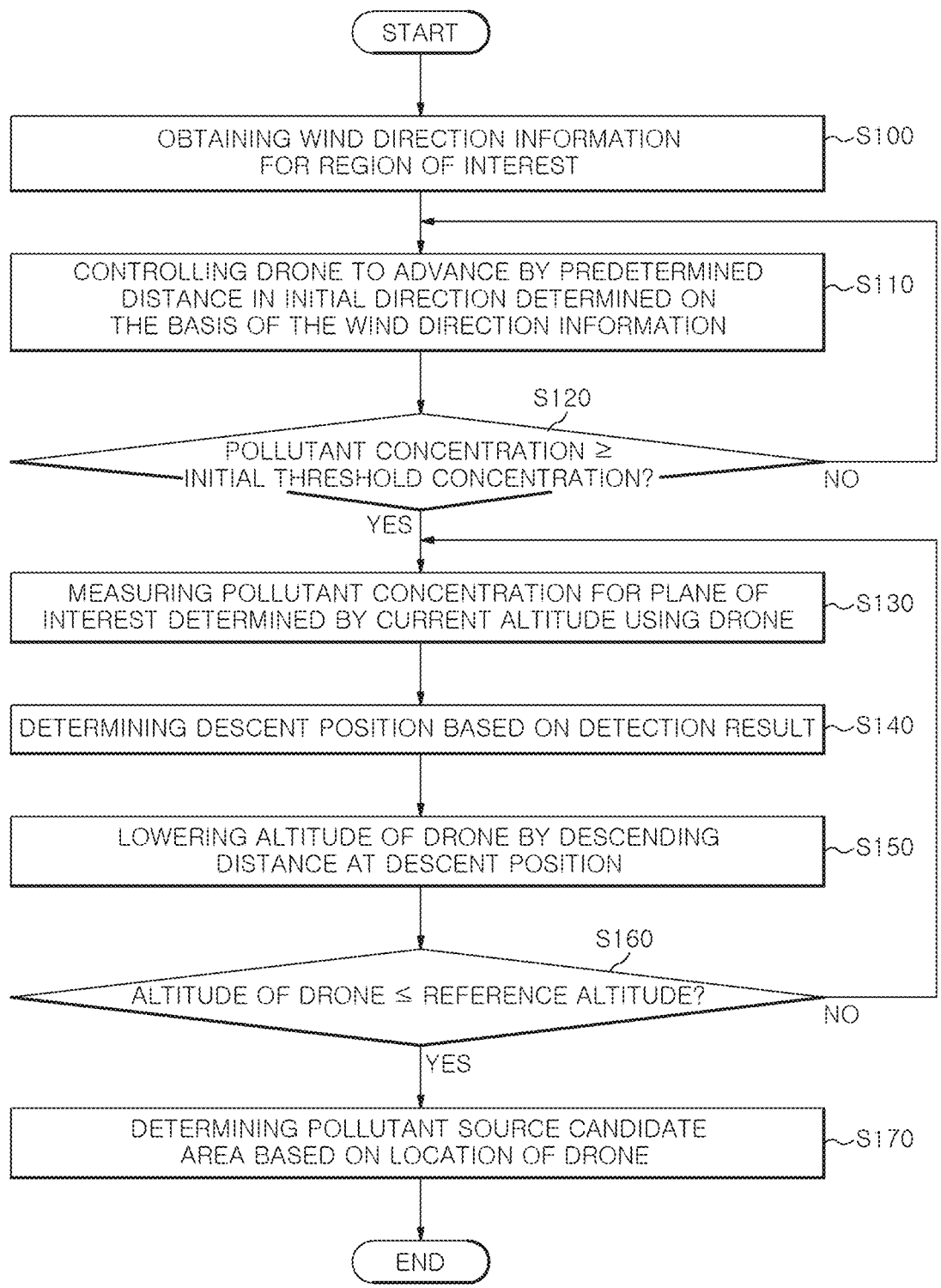
FIG. 4 is a flowchart of a method for determining the location of a pollutant source according to one embodiment of the present disclosure.

FIG. 4 is a flowchart of the method for determining the location of a pollutant source according to one embodiment of the present disclosure.

First, the pollutant source location determining apparatus 1 obtains wind direction information for the region of interest (S100). Here, the region of interest refers to the region where the pollutant source is expected to exist and may include the area where there is a chemical pollutant cloud formed by chemical substances discharged from the pollutant source.

The pollutant source location determining apparatus 1 can identify a region of interest including the chemical pollutant cloud using the drone 100. The pollutant source location determining apparatus 1 according to one embodiment may identify a region of interest from an image obtained by a camera mounted on the drone 100. The pollutant source location determining apparatus 1 according to another embodiment may identify a region of interest based on a value obtained by a sensor for identifying a region of interest which is installed at the drone 100.

Once the region of interest is identified, the drone 100 may obtain wind direction information at a predetermined point in the region of interest. The drone 100 according to one embodiment may acquire the information of the wind direction at the center in the region of interest, and the drone 100 according to another embodiment may acquire the information of the wind direction at the center of gravity in the region of interest.

The drone 100 can acquire the wind direction for the region of interest using the loaded lidar 140. The process for obtaining the wind direction by the lidar 140 is as described in FIG. 2.

Then, the pollutant source location determining apparatus 1 controls the drone 100 to advance by a predetermined distance in an initial direction determined on the basis of the wind direction information (S110). To this end, the pollutant source location determining apparatus 1 may first determine the initial direction. Hereinafter, a process for determining the initial direction for the drone 100 will be described with reference to FIG. 5.

Figure 5:
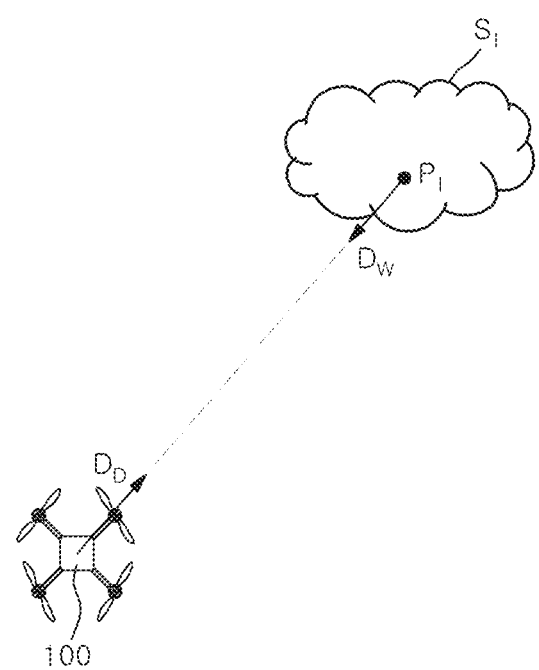
FIG. 5 explains a process for determining an initial movement direction of a drone according to one embodiment of the present disclosure.

FIG. 5 is a view for explaining an initial direction determination process for a drone according to one embodiment.

Referring to FIG. 5, the drone 100 obtains the wind direction $D_W$ for the center point $P_I$ in the region of interest $S_I$. When the wind direction $D_W$ is acquired, the drone 100 can fly up to a predetermined initial altitude. In this case, the initial altitude means an altitude in accordance with a plane in the region of interest to be explored first, and an initial altitude according to one embodiment may be determined to be 10 m from the ground.

Then, the pollutant source location determining apparatus 1 determines the direction opposite to the wind direction $D_W$ as the initial direction. That is, the initial direction may be parallel to the wind direction $D_W$ and may have a sign opposite to that of the wind direction $D_W$.

When the initial direction is determined, the drone 100 takes the initial direction as an advance direction $D_D$ thereof and advances in the initial direction by a predetermined distance. Here, the predetermined distance means a distance determined in advance to detect a change in the pollutant concentration.

Referring back to FIG. 4, after the drone 100 travels a predetermined distance, the pollutant source location determining apparatus 1 checks whether the pollutant concentration measured by the drone 100 is equal to or greater than an initial threshold concentration (S120). Here, the initial threshold concentration means the lowest chemical concentration that can be detected when the drone 100 is present in the region of interest including the chemical pollutant cloud. For this purpose, the drone 100 can detect the chemical concentration at the current position using the mounted chemical sensor 130.

If the measured pollutant concentration is less than the initial threshold concentration, the drone 100 can continue to travel a predetermined distance in the initial direction.

On the other hand, if the measured pollutant concentration is equal to or greater than the initial threshold concentration, the pollutant source location determining apparatus 1 can measure the pollutant concentration for the plane of interest determined based on the current altitude of the drone 100 using the drone 100 (S130). The fact that the pollutant concentration is equal to or greater than the initial threshold concentration means that the drone 100 has entered the region of interest.

Here, the plane of interest means a plane corresponding to the current altitude of the drone 100 in the region of interest. If it is determined that the pollutant concentration measured by the drone 100 traveling in the initial direction is equal to or greater than the initial threshold concentration, the drone 100 can measure the concentration of pollution for the plane of interest determined from the initial altitude.

Hereinafter, a pollutant concentration measuring process for a plane of interest will be described with reference to FIGS. 6 and 7.

Figure 6:
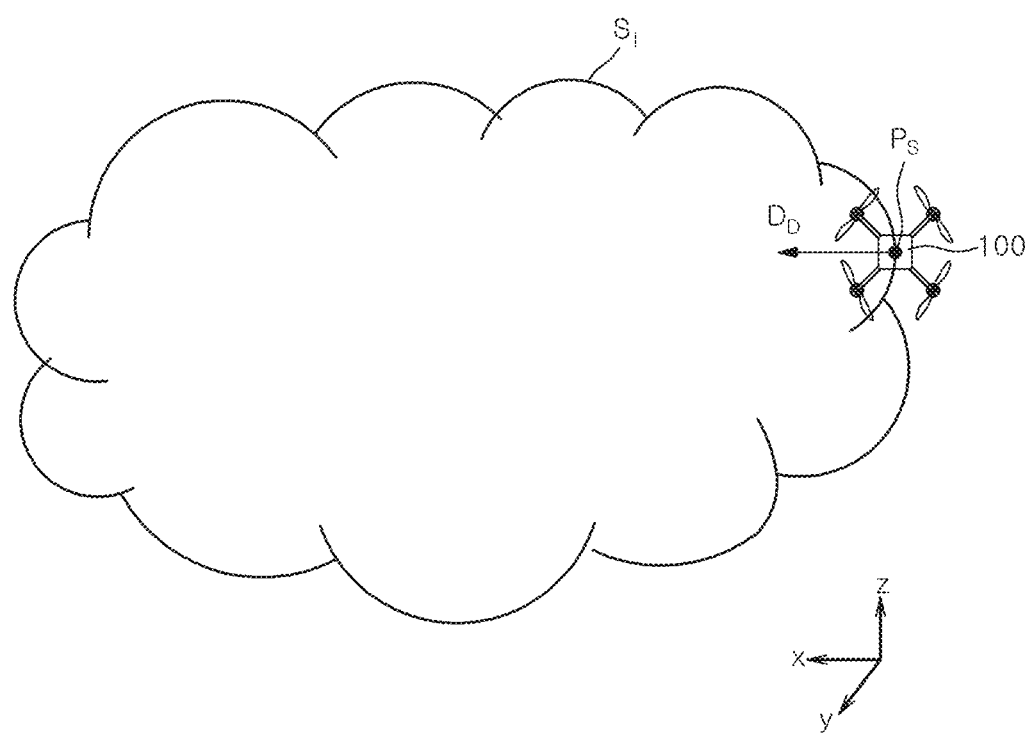
FIG. 6 explains a pollutant concentration measuring process in a first traveling direction for a plane of interest according to one embodiment of the present disclosure.
Figure 7:
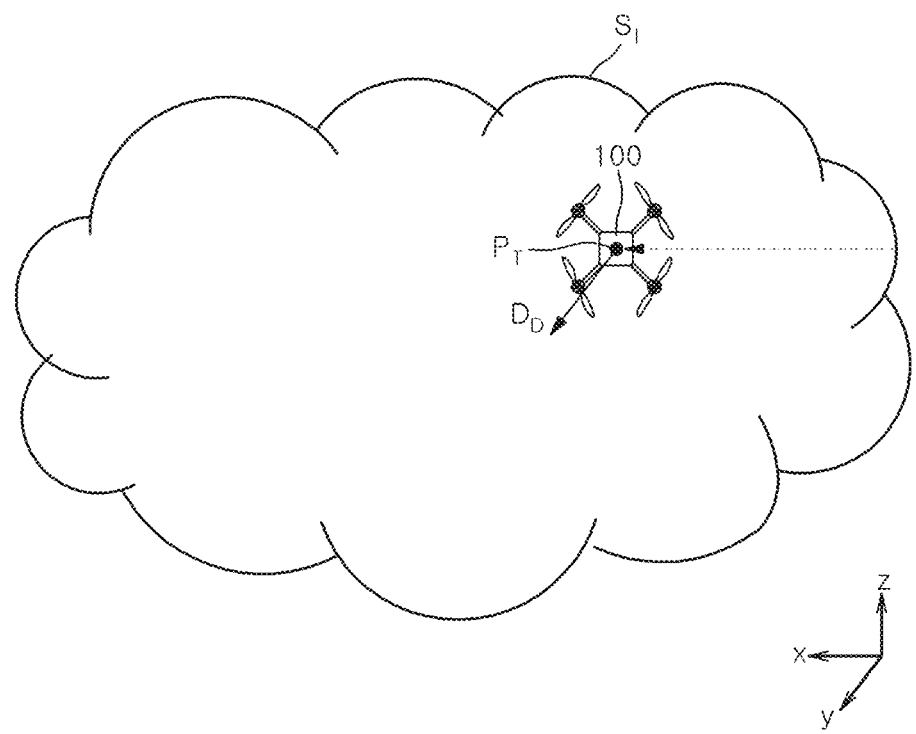
FIG. 7 explains a pollutant concentration measuring process in a second traveling direction for the plane of interest.

FIG. 6 is a view for explaining a pollutant concentration measuring process in a first traveling direction with respect to a plane of interest according to one embodiment. FIG. 7 is a view for explaining a pollutant concentration measuring process in a second traveling direction with respect to a plane of interest according to one embodiment.

If it is determined that the drone 100 has entered the region of interest, the pollutant source location determining apparatus 1 controls the drone 100 to advance in the first traveling direction. Here, the first traveling direction means the opposite direction to the identified wind direction, that is, the initial direction.

The drone 100 can measure the concentration of pollution through the chemical sensor 130 while traveling in the first traveling direction as the advance direction $D_D$. Referring to FIG. 6, the drone 100 advances from an entry point $P_S$ for the region of interest in the first traveling direction as the advance direction $D_D$, and the first traveling direction may be the x-axis direction. At this time, the drone 100 may measure the pollutant concentration at predetermined time intervals while traveling in the advance direction $D_D$, or may measure the pollutant concentration whenever it travels a predetermined distance.

Then, the pollutant source location determining apparatus 1 can determine as a turning position a position at which the highest pollution concentration is detected by the drone 100 traveling in the first traveling direction in the detection area.

When the turning position is determined, the drone 100 turns at the turning position and travels in the second traveling direction, as the advance direction $D_D$, perpendicular to the first traveling direction. Referring to FIG. 7, the drone 100 turns at the turning position $P_T$ and travels in the second traveling direction as the advance direction $D_D$. As shown in FIG. 6, when the first traveling direction corresponds to the x-axis, the second traveling direction may correspond to the y-axis perpendicular to the x-axis.

While traveling in the second traveling direction, the drone 100 can measure the pollutant concentration along the second traveling direction in the region of interest. At this time, the drone 100 may measure the pollutant concentration at predetermined time intervals while traveling in the advance direction $D_D$, or may measure the pollutant concentration whenever it travels a predetermined distance.

Referring again to FIG. 4, the pollutant source location determining apparatus 1 determines a descent position based on the detection result (S140). Here, the descent position means a position determined to be closest to the pollutant on the plane of interest. Specifically, the pollutant source location determining device 1 determines as the descent position a position where the highest pollutant concentration is detected by the drone 100 traveling in the second traveling direction as the advance direction $D_D$ in the detection area.

When the descent position is determined, the pollutant source location determining apparatus 1 lowers the altitude of the drone 100 from the descent position by the descending distance (S150). Here, the descending distance means a predetermined distance to change the plane of interest in the region of interest. Hereinafter, with reference to FIG. 8, a process for lowering the altitude of the drone 100 from the descent position will be described.

Figure 8:
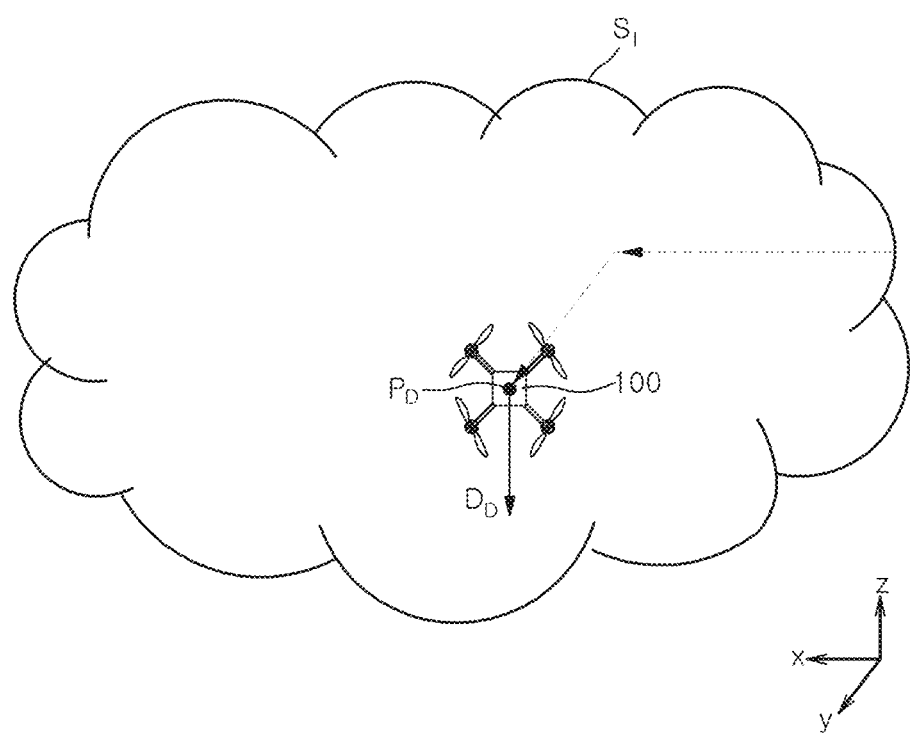
FIG. 8 explains a process for lowering the altitude of the drone from the descent position.

FIG. 8 is a view for explaining a process for lowering the altitude of the drone 100 from the descent position.

The pollutant source location determining apparatus 1 can determine as the descent position a position at which the highest pollutant concentration is detected by the drone 100 travelling in the second traveling direction as the advance direction $D_D$. That is, the descent position may indicate a position at which the highest pollutant concentration is detected in the second traveling direction from the turning position at which the highest pollutant concentration is detected in the first traveling direction in the region of interest.

When the descent position is determined, the drone 100 at the descent position can lower the altitude by the descending distance. Referring to FIG. 8, the drone 100 descends from the descent position $P_D$ by the descending distance in a descending direction as the advance direction $D_D$ of the drone 100. At this time, the descending direction may be the z-axis direction or the opposite direction.

Referring again to FIG. 4, after the altitude of the drone 100 is lowered, the pollutant source location determining apparatus 1 confirms whether the altitude of the drone 100 is equal to or greater than a reference altitude (S160). Here, the reference altitude means the maximum altitude among altitudes at which the ground can be determined.

If the altitude of the drone 100 exceeds the reference altitude, the pollutant source location determining apparatus 1 determines that the drone 100 has not reached the ground. Then, the pollutant source location determining apparatus 1 detects the pollutant concentration for the plane of interest determined based on the current altitude in the region of interest again. By repeating this, the concentration of pollution in the region of interest can be detected on the altitude basis.

On the other hand, if the altitude of the drone 100 is equal to or less than the reference altitude, the pollutant source location determining apparatus 1 determines that the drone 100 has reached the ground. Hereinafter, a process for determining that the drone 100 has reached the ground will be described with reference to FIG. 9.

Figure 9:
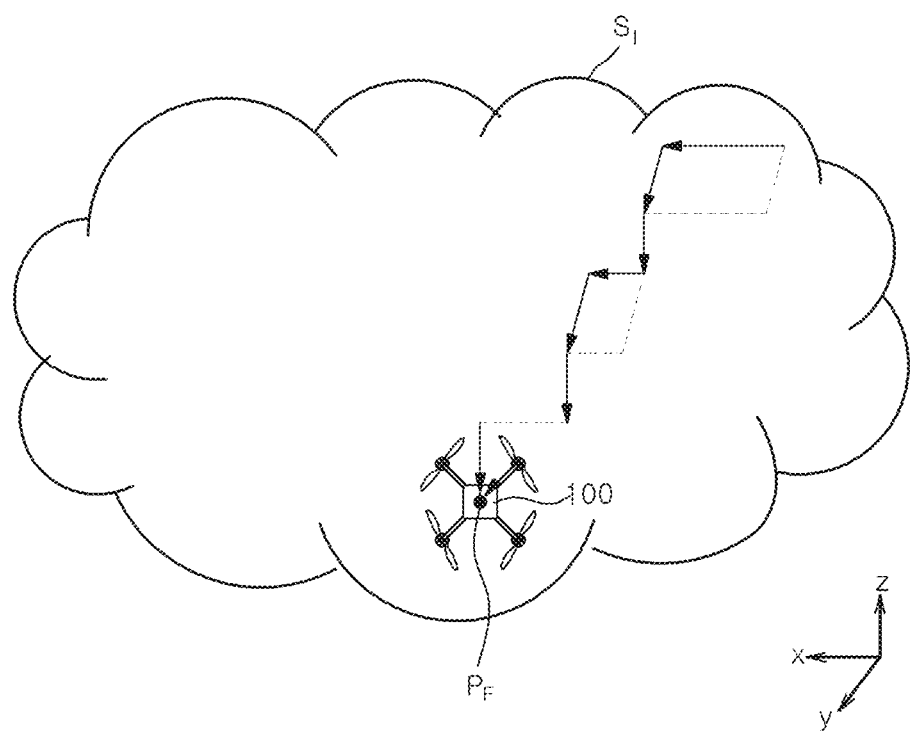
FIG. 9 explains a process for determining that the drone has reached the ground.

FIG. 9 is a view for explaining a process for determining that the drone has reached the ground.

The pollutant source location determining apparatus 1 newly sets the plane of interest based on the altitude of the drone 100 whenever the drone 100 descends by the descending distance, and detects the chemical concentration in the plane of interest which has been newly set. By repeating this, it is possible to detect the chemical concentration for the entire region of interest.

While repeating the above process, the pollutant source location determining apparatus 1 can confirm whether the altitude of the drone 100 is less than or equal to the reference altitude whenever the drone 100 at the descent position descends by the descent distance. Finally, when the altitude of the drone 100 falls below the reference altitude, the pollutant source location determining apparatus 1 can determine that the drone 100 has reached the ground. In the case of FIG. 9, it can be confirmed that the drone 100 reaches the final descent position $P_F$ above the ground.

After the drone 100 reaches the ground, the pollutant source location determining apparatus 1 determines a pollutant source candidate area (an area where the pollutant source may exist) based on the location of the drone 100 (S170). Hereinafter, a process for determining a pollutant source candidate area will be described with reference to FIGS. 10 and 11.

Figure 10:
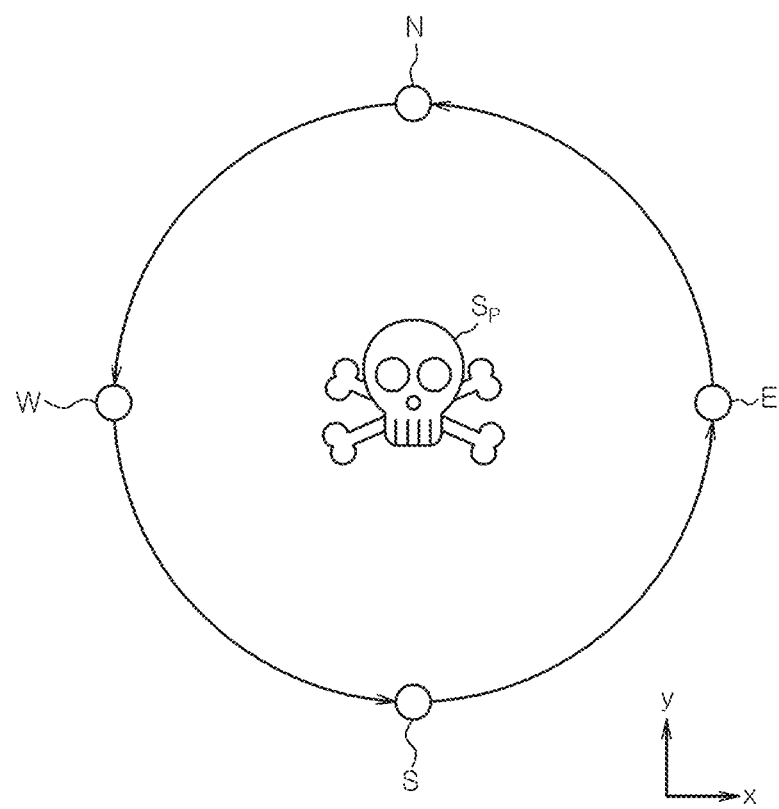
FIGS. 10 and 11 show processes for determining a pollutant source candidate area according to different embodiments of the present disclosure.
Figure 11:
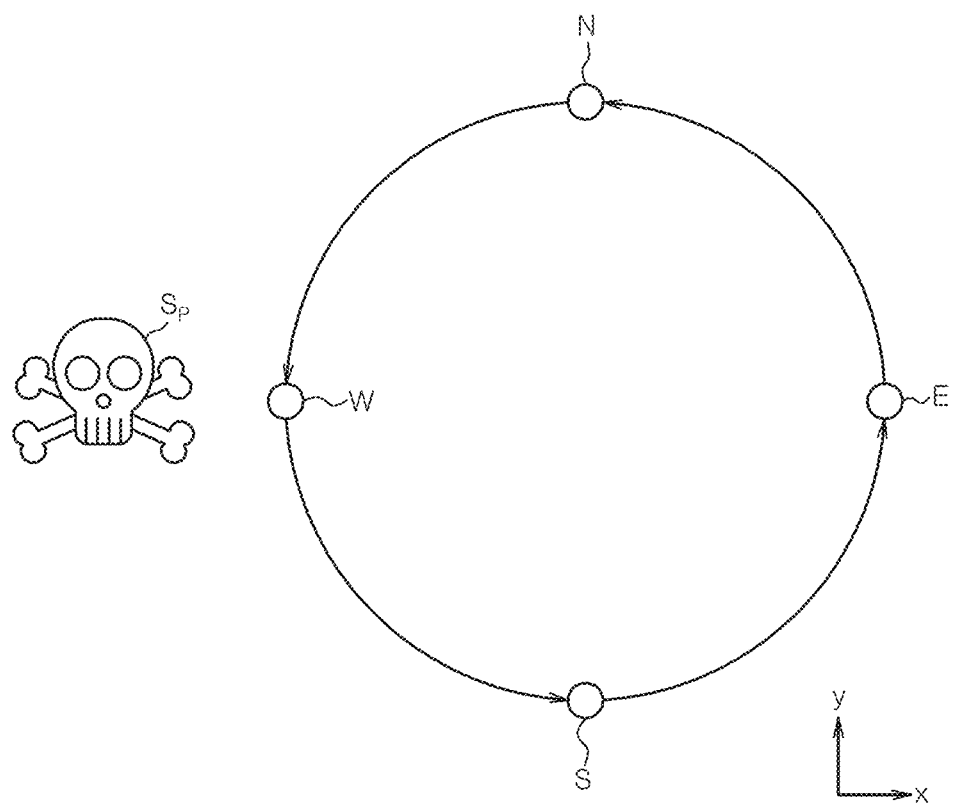

FIGS. 10 and 11 show processes for determining a pollutant source candidate area according to different embodiments of the present disclosure.

The pollutant source location determining apparatus 1 can determine a pollutant source candidate area based on the position of the drone 100, that is, the final descent position. To this end, the pollutant source location determining apparatus 1 according to one embodiment may determine a center position. At this time, the center position means a position spaced from the final descent position by a predetermined radial distance.

Then, the pollutant source location determining apparatus 1 can measure the pollutant concentration at a plurality of detection positions spaced from the determined center position by the predetermined radial distance. Referring to FIG. 10, the pollutant source location determining apparatus 1 determines four detection positions N, W, S and E spaced by the predetermined radial distance from the center position, and the drone 100 explores the respective detection positions N, W, S and E. At this time, the drone 100 according to one embodiment can measure the pollutant concentration while moving along the circumference separated by the predetermined radial distance from the center position. In FIG. 10, the case of detecting the pollutant concentration while the drone 100 moves in the counterclockwise direction is exemplified. However, it is also possible for the drone 100 to measure the pollutant concentration while moving in the clockwise direction.

If the pollutant concentration detected at each of the plurality of detection locations is equal to or greater than a predetermined reference concentration, the pollutant source location determining apparatus 1 can determine an area within the predetermined radial distance from the center position as the pollutant source candidate area. Here, the reference concentration means the minimum pollutant concentration to be detected when the pollutant source is located in the vicinity. In FIG. 10, a circle formed by the plurality of detection positions N, W, S and E may be a pollutant source candidate area in which a pollutant source Sp exists.

On the other hand, if at least a part of the pollution concentrations detected at the plurality of detection positions is less than the predetermined reference concentration, the pollutant source location determining apparatus 1 determines a pollutant source candidate area based on the detection positions at which the pollutant concentration equal to or greater than the predetermined reference concentration has been detected. As described above, if the measured pollutant concentration is higher than the reference concentration, there is a high possibility that a pollutant exists in the vicinity thereof. Therefore, it is possible to determine a pollutant source candidate area only based on the corresponding detection positions.

If there is the pollutant source Sp exists outside the circle formed by the plurality of detection positions N, W, S and E as shown in FIG. 11, only the pollutant concentration measured at the detection positions W and N or S may be higher than the reference concentration. In this case, the pollutant source location determining apparatus 1 according to one embodiment sets a new center point at a position spaced by the predetermined radial distance from the detection positions W and N or S, at which the pollutant concentration equal to or greater than the reference concentration has been detected, and it is possible to determine a pollutant source candidate area by detecting the pollutant concentration at the newly set detection positions.

If it is not possible to determine a pollutant source candidate area even though the pollution concentration is detected at the new detection positions, the pollution source location determining apparatus 1 can repeatedly perform the above process. If a predetermined time has elapsed during the detection of the pollutant concentration for determining the pollutant source candidate area, the pollutant source location determining apparatus 1 may select, among the pollutant concentrations detected at the entire detection positions, some of the pollutant concentrations in descending order and determine the pollutant source candidate area based on the detection positions for the selected pollutant concentrations.

Alternatively, the pollutant source location determining apparatus 1 according to another embodiment may determine, as the pollutant source candidate area, an area within a predetermined distance from the detection position at which the pollutant concentration equal to or higher than the reference concentration has been detected.

The above-described apparatus and method for determining a pollutant source location can determine the location of the pollutant source using the drone, thereby making it possible to more safely explore for a chemical pollutant cloud.

Further, by exploring the chemical pollutant cloud based on the plane determined in accordance with the altitude of the drone, the search accuracy for the chemical pollutant cloud can be increased. As a result, it is possible to correctly determine the location of the pollutant source in the chemical pollutant cloud.

Logical blocks, modules or units described in connection with embodiments disclosed herein can be implemented or performed by a computing device having at least one processor, at least one memory and at least one communication interface. The elements of a method, process, or algorithm described in connection with embodiments disclosed herein can be embodied directly in hardware, in a software module executed by at least one processor, or in a combination of the two. Computer-executable instructions for implementing a method, process, or algorithm described in connection with embodiments disclosed herein can be stored in a non-transitory computer readable storage medium.

The above description is merely exemplary description of the technical scope of the present disclosure, and it will be understood by those skilled in the art that various changes and modifications can be made without departing from original characteristics of the present disclosure. Therefore, the embodiments disclosed in the present disclosure are intended to explain, not to limit, the technical scope of the present disclosure, and the technical scope of the present disclosure is not limited by the embodiments. The protection scope of the present disclosure should be interpreted based on the following claims and it should be appreciated that all technical scopes included within a range equivalent thereto are included in the protection scope of the present disclosure.

What is claimed is:

1. A method for determining a location of a pollutant source, the method comprising:
    obtaining wind direction information for a region of interest;
    measuring pollutant concentrations for a first plane of interest in the region of interest with a movement determined based on the wind direction information using a drone equipped with a chemical sensor, the first plane of interest being determined based on a current altitude of the drone;
    lowering by a predetermined descending distance an altitude of the drone from a descent position on the first plane of interest determined on the basis of a result of said measuring; and
    determining a pollutant source candidate area based on a lowered location of the drone after said lowering if the lowered altitude of the drone is equal to or less than a predetermined reference altitude,
    wherein the determining comprises:
        determining a center position located within a predetermined distance from the lowered location;
        measuring pollutant concentrations at a plurality of detection positions spaced from the center position;
        determining if there is a low concentration detection position among the plurality of detection positions, of which the pollutant concentration is less than a predetermined pollutant concentration;
        when determined that there is no low concentration detection position, determining an area formed based on the plurality of detection positions as the pollutant source candidate area;
        when determined that there is the low concentration detection position, determining a new center position moved from the center position in a direction away from the low concentration detection position; and
        further measuring pollutant concentrations at a plurality of new detection positions spaced from the new center position.

2. The method of claim 1, further comprising:
    measuring pollutant concentrations for a second plane of interest determined based on the lowered altitude of the drone if the lowered altitude of the drone exceeds the reference altitude.

3. The method of claim 1, wherein said measuring pollutant concentrations includes:
    advancing the drone in a first traveling direction determined on the basis of the wind direction information to measure the pollutant concentration;
    determining as a turning position a position at which the highest pollution concentration is detected by the drone among first positions at which the drone measures the pollutant concentrations while moving in the first traveling direction; and
    turning the drone at the turning position and advancing the drone in a second traveling direction substantially perpendicular to the first traveling, direction to measure the pollutant concentration,
    wherein the movement includes a movement in the first traveling direction and a movement in the second traveling direction.

4. The method of claim 3, wherein said lowering the altitude of the drone includes:
    determining as the descent position a position at which the highest pollution concentration is detected by the drone among second positions at which the drone measures the pollutant concentrations while moving in the second traveling direction; and
    lowering the altitude of the drone from the descent position by the predetermined descending distance.

5. The method of claim 1, wherein said determining the pollutant source candidate area based on the pollutant concentrations at the plurality of detection positions includes:
    obtaining a gradient of the pollutant concentrations at the plurality of detection positions; and
    determining the pollutant source candidate area further based on the obtained pollutant concentration gradient.

6. The method of claim 1, wherein the plurality of detection positions are spaced apart by a predetermined radial distance from the center position.

7. The method of claim 6, wherein the plurality of detection positions comprise four detection positions substantially equally spaced apart from each other along a circle centered on the center position.

8. The method of claim 7, wherein the drone measures pollutant concentrations while moving in a counterclockwise or clockwise direction along the circumference.

9. The method of claim 7, wherein the determining comprises determining an area within the predetermined radial distance from the center position as the pollutant source candidate area in response to the pollutant concentration detected at each of the plurality of detection positions is equal to or greater than a predetermined reference concentration.

10. An apparatus for determining a location of a pollutant source, the apparatus comprising:
    a drone equipped with a chemical sensor for detecting concentration of pollution; and
    a control unit configured to control the drone,
    wherein the control unit is configured to control the drone to measure pollutant concentrations for a first plane of interest in a region of interest with a movement determined based on wind direction information with respect to the region of interest, the first plane of interest being determined based on a current altitude of the drone, lower an altitude of the drone from a descent position on the first plane of interest determined on the basis of the measurement result by a predetermined descending distance, and determine a pollutant source candidate area based on a lowered location of the drone if the lowered altitude of the drone is equal to or less than a predetermined reference altitude,
    wherein the control unit is further configured to:
        determine a center position located within a predetermined distance from the lowered location;
        measure pollutant concentrations at a plurality of detection positions spaced from the center position;
        determine if there is a low concentration detection position among the plurality of detection positions, of which the pollutant concentration is less than a predetermined pollutant concentration;
        when determined that there is no low concentration detection position, determine an area formed based on the plurality of detection positions as the pollutant source candidate area;
        when determined that there is the low concentration detection position, determine a new center position moved from the center position in a direction away from the low concentration detection position; and measure pollutant concentrations at a plurality of new detection positions spaced from the new center position.

11. The apparatus of claim 10, wherein the drone comprises:
a lidar configured to obtain the wind direction information with respect to the region of interest.

12. The apparatus of claim 10, wherein the plurality of detection positions are spaced apart by a predetermined radial distance from the center position.

13. The apparatus of claim 12, wherein the plurality of detection positions comprise four detection positions substantially equally spaced apart from each other along a circle centered on the center position.

14. The apparatus of claim 12, wherein the plurality of detection positions form a circumference around the center position.

15. The apparatus of claim 14, wherein the control unit is configured to determine an area within the predetermined radial distance from the center position as the pollutant source candidate area in response to the pollutant concentration detected at each of the plurality of detection positions is equal to or greater than a predetermined reference concentration.

16. A non-transitory computer-readable storage medium storing executable instructions, wherein the instructions, when executed by a processor, cause the processor to perform a method for determining a location of a pollutant source, the method comprising:
obtaining wind direction information for a region of interest;
measuring pollutant concentrations for a first plane of interest in the region of interest with a movement determined based on the wind direction information using a drone equipped with a chemical sensor, the first plane of interest being determined based on a current altitude of the drone;
lowering by a predetermined descending distance an altitude of the drone from a descent position on the first plane of interest determined on the basis of a result of said measuring; and
determining a pollutant source candidate area based on a lowered location of the drone after said lowering if the lowered altitude of the drone is equal to or less than a predetermined reference altitude,
wherein the determining comprises:
determining a center position located within a predetermined distance from the lowered location;
measuring pollutant concentrations at a plurality of detection positions spaced from the center position;
determining if there is a low concentration detection position among the plurality of detection positions, of which the pollutant concentration is less than a predetermined pollutant concentration;
when determined that there is no low concentration detection position, determining an area formed based on the plurality of detection positions as the pollutant source candidate area;
when determined that there is the low concentration detection position, determining a new center position moved from the center position in a direction away from the low concentration detection position; and
further measuring pollutant concentrations at a plurality of new detection positions spaced from the new center position.

* * * * *